United States Patent [19]

Olms

[11] Patent Number: 5,137,475

[45] Date of Patent: Aug. 11, 1992

[54] MEDICAL ELECTRICAL CONNECTOR FOR FLEXIBLE ELECTRODES

[75] Inventor: Harald O. Olms, El Toro, Calif.

[73] Assignee: Tronomed, Inc., San Juan Capistrano, Calif.

[21] Appl. No.: 708,976

[22] Filed: May 31, 1991

[51] Int. Cl.$^5$ .............................................. H01R 4/28
[52] U.S. Cl. ..................................... 439/725; 439/909
[58] Field of Search ................ 439/296, 347, 725–729, 439/775, 783, 835–837, 863, 909; 128/639, 640, 641

[56] References Cited

U.S. PATENT DOCUMENTS

| | | | |
|---|---|---|---|
| 4,061,408 | 12/1977 | Bast et al. | |
| 4,555,155 | 11/1985 | Drake | 439/838 X |
| 4,700,997 | 10/1987 | Strand | 439/863 X |
| 4,702,256 | 10/1987 | Robinson et al. | 439/729 X |
| 4,761,143 | 8/1988 | Owens et al. | 439/372 |
| 4,768,969 | 9/1988 | Bauer et al. | 439/725 X |
| 4,797,125 | 1/1989 | Malana | 439/729 |
| 4,842,558 | 6/1989 | Strand | 439/863 X |

Primary Examiner—Larry I. Schwartz
Assistant Examiner—Khiem Nguyen
Attorney, Agent, or Firm—Price, Gess & Ubell

[57] ABSTRACT

A biomedical electrical connector that includes a lower body member and an upper actuator member is provided. The body member has a front end of a curvilinear configuration and a rear platform component. The platform component has guide ribs disposed on either side that extend parallel to the longitudinal axis of the body. An actuator member has downwardly-projecting guide flanges on either side of a coupling portion that extend parallel to its longitudinal axis. Each flange includes a groove in its interior side of a complementary configuration to the guide ribs for slidably coupling the actuator substantially parallel to the longitudinal axis of the body. The actuator has a front end of a curvilinear configuration cantilevered from the coupling portion. A sinusoidal interface is defined between the actuator's curvilinear front end and the body' curvilinear front end when the actuator is slid generally forwardly in relation to the body to an overcenter position. A portion of a flexible electrode may be frictionally engaged by the sinusoidal interface of the body and the actuator and brought into electrical contact with a terminal. Teeth of the terminal extend slightly into the portion of flexible electrode to prevent the connector from detaching from the flexible electrode and for conductively coupling the terminal to the electrode.

19 Claims, 2 Drawing Sheets

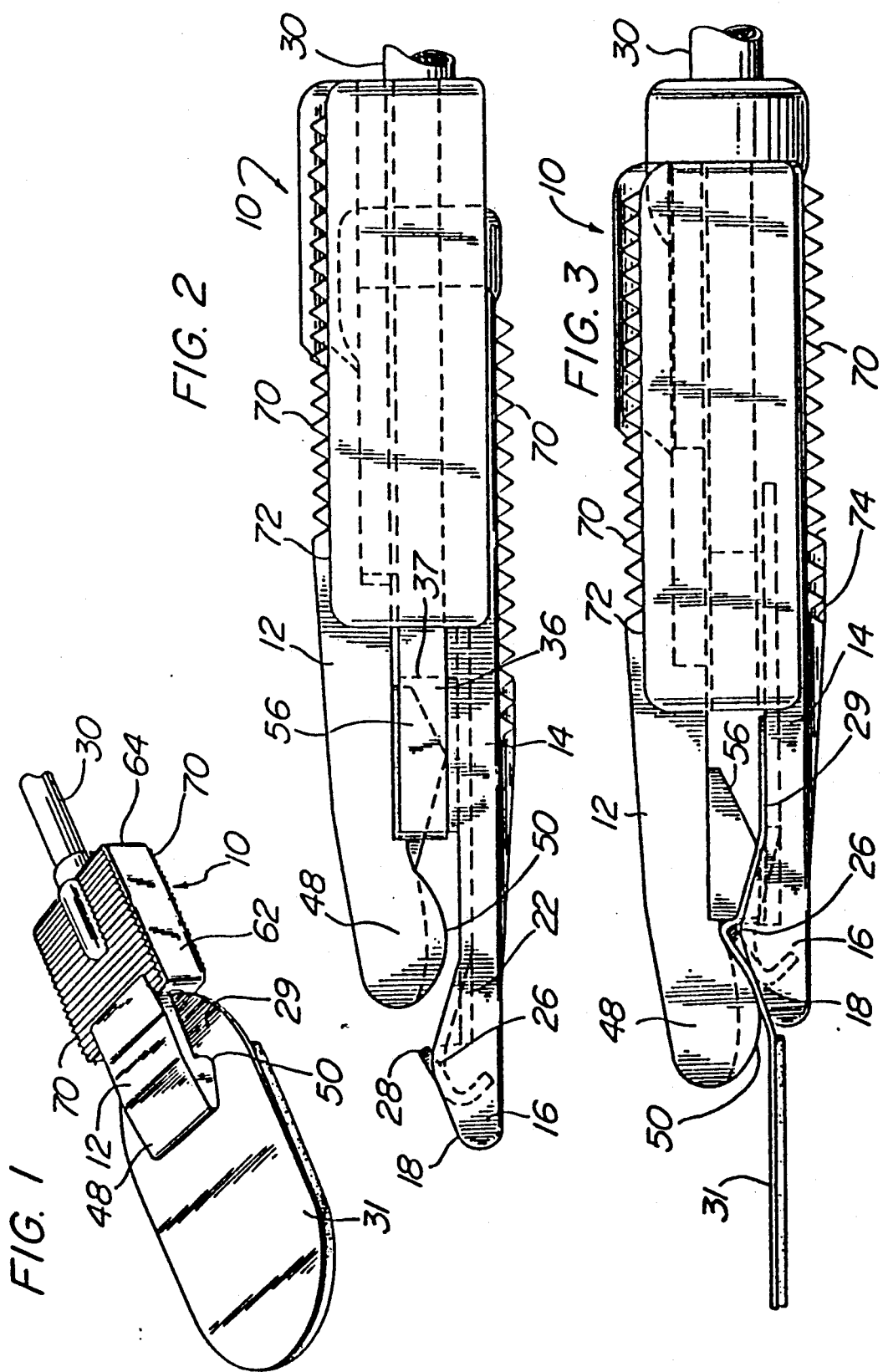

MEDICAL ELECTRICAL CONNECTOR FOR FLEXIBLE ELECTRODES

BACKGROUND OF THE INVENTION

1. Field of the Invention

The subject invention relates generally to medical electrical connectors and, more particularly, to a low profile medical electrical connector for detachably coupling a flexible electrode to an electrical wire.

2. Description of Related Art

Biomedical electrodes are used for transcutaneous monitoring of variations in electrical potential associated with muscular activity such as a heartbeat and for grounding patients during electrosurgery. The medical industry has used a large number of electrical and electrode connectors for attachment to flexible substrate electrodes on patients. This field is relatively crowded and designs are usually controlled by, first, a requirement for a secure fastening of an electrode connector to an electrode, since it can be part of a life support system, second, by the economics of providing a relatively inexpensive, reusable electrode connector, and third, by the need for an electrical connector that is relatively easy to operate.

U.S. Pat. No. 4,797,125 is directed to a medical electrode connector for flexible substrate electrodes and includes a first base member having a receptacle and a second member movably attached to the first member and having a prong member of a configuration compatible with movement into the receptacle. An electrical contact plate is provided on one of the receptacle and prong members for providing an electrical contact with the flexible electrode when the prong member is positioned on one side of the electrode and the receptacle is positioned on the other side. The prong member forces the electrode to be deformed and to be positioned within the receptacle, to thereby provide a positive locking electrical contact.

U.S. Pat. No. 4,768,969 discloses a camming structure for providing an overcenter lock of a flexible electrode.

U.S. Pat. No. 4,761,143 discloses an electrode clip having a slide actuator that will cam a pivoting contact body to force a flexible electrode into contact with spring members to form an electrical contact.

U.S. Pat. No. 4,061,408 discloses another form of overcentered toggle mechanism for clamping a jaw member onto a flexible electrode.

U.S. Pat. No. 4,700,997 discloses a sliding actuator to close a spring clamp onto a flat tabbed electrode.

Finally, U.S. Pat. No. 4,842,558 discloses an electrical connector having an actuator that is slidable diagonally relative to a longitudinal passageway between an open position and a wedge position for holding a flexible electrode.

As can be appreciated, there exists a need for a reusable medical electrical connector that is inexpensive to manufacture and securely attaches to flexible substrate electrodes of different designs and configurations. The prior art is still seeking to optimize such a design.

SUMMARY OF THE INVENTION

It is therefore an object of the present invention to provide an improved medical electrical connector that responds to the requirements of a reusable low profile connector in an economical manner; and It is another object of the invention to provide an electrical connector that may be easily attached by an operator to flexible thin biomedical electrodes of varying designs and configurations.

These and other objects and advantages of the present invention are achieved by providing an electrical connector formed of two components that can be readily manufactured by injection molding and assembled together. A lower body member has a front end with a curvilinear configuration for defining a first camming surface. The curvilinear front end is cantilevered from a rear platform component that mounts an electrical lead wire. The platform includes guide ribs disposed on either side that extend parallel to the longitudinal axis of the body member.

A terminal is connected to the lead wire and includes a plurality of teeth projecting outwardly from an apex of the first camming surface and adjacent to a notch in the first camming surface. The teeth extend away from the body member's curvilinear front end at an acute angle to the longitudinal axis of the body member.

An upper actuator component has downwardly-projecting guide flanges located on either side of a coupling portion that extend parallel to the longitudinal axis. Each flange includes a groove in its interior side of a complementary configuration to the guide ribs to slidably engage the guide ribs of the body platform, for slidably coupling the coupling portion of the actuator component substantially parallel to the body member. The actuator component has a curvilinear front end defining a second camming surface. When the actuator is slid to a forwardmost position in relation to the body member, the second camming surface extends over the center of the first camming surface for forming a sinusoidal interface defined between the curvilinear front end of the actuator and the body member's curvilinear front end. A stop is disposed adjacent to the actuator's curvilinear front end for locking the actuator in the overcenter position.

A connector portion of a flexible electrode is placed between the front end of the actuator and the front end of the body member when the actuator is in a retracted position. The actuator is then slid along a longitudinal axis to its forwardmost position with the respective front ends of the actuator and body member flexing to grasp the electrode. The connector portion of the flexible electrode is frictionally engaged by the sinusoidal interface formed by the overcenter locking position, and brought into electrical contact with the terminal. The teeth of the terminal will extend slightly into the electrode for enhancing the electrical contact and will prevent the connector both from detaching from the flexible electrode and from rotating about the sinusoidal interface. The configuration of the sinusoidal interface of the electrical connector enables the electrical connector to attach to a large number of flexible electrodes having different designs and configurations.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 is a perspective view of the medical electrical connector;

FIG. 2 is a side view showing the preferred embodiment of the present invention in an open position;

FIG. 3 is a side view showing the preferred embodiment in a closed position;

DESCRIPTION OF THE PREFERRED EMBODIMENTS

The following description is provided to enable any person skilled in the medical electrical connector art to make and use the invention and sets forth the best modes contemplated by the inventor for carrying out his invention. Various modifications, however, will remain readily apparent to those skilled in these arts, since the generic principles of the present invention have been defined herein.

Referring to FIGS. 1 through 3, a preferred embodiment of an electrical connector 10, constructed according to the principles of the present invention, is shown. The electrical connector 10 comprises basically two components, an actuator 12 slidably coupled along a longitudinal axis to a substantially flat elongated body 14.

Figure 5:
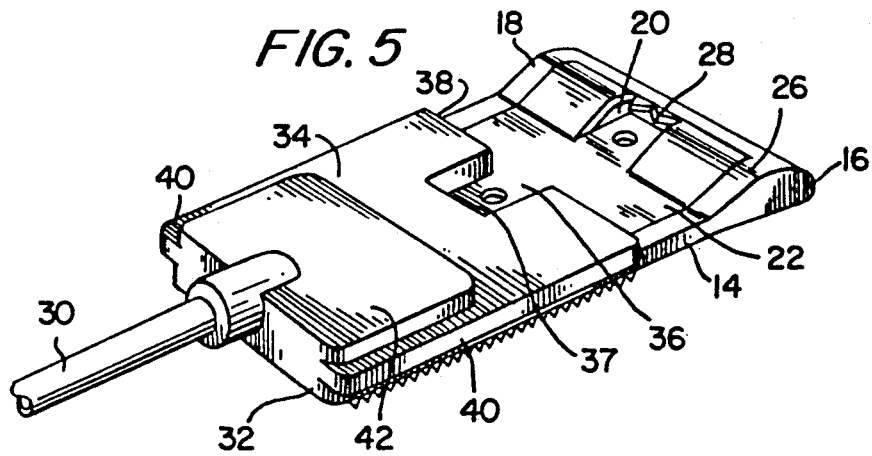
FIG. 5 is a top perspective view of a body of the preferred embodiment.

Referring now to FIG. 5, there is shown a top perspective view of the body 14 having a front end 16 of a curvilinear configuration. A top portion of the curvilinear front end 16 defines a first camming surface 18. The first camming surface 18 has a notch 20 located in its center region. The body 14 may be molded from any suitable rigid medical grade plastic, such as an ABS plastic. The body 14 may also be molded from an electrically conductive medical grade plastic that is X-ray translucent to substantially reduce the electrical connector's image in any X-ray pictures of a patient.

An electrically conductive terminal 22 is disposed on a top surface of the body 14. The terminal 22 extends from just beyond an apex 26 of the first camming surface 18 and along the length of the body 14. The terminal 22 has a plurality of teeth 28 that project outwardly from the first camming surface's apex 26 and at an acute angle to the longitudinal axis of the body 14. The teeth 28 are located adjacent to the notch 20.

The terminal 22 is coupled to an electrical lead wire 30 at a second end 32 of the body 14, for conducting electrical potential from a flexible electrode 31 (shown in FIGS. 1, 3, and 4) through the conductive terminal 22, to a monitor (not shown). The lead wire 30 may enclose a thin ribbon of copper that has been sized so as not to interfere with X-ray photography. The terminal 22 may be made of any suitable electrically conductive material, such as beryllium, carbon, or copper. It may be desired to make the terminal 22 out of a suitable electrically conductive, X-ray translucent material, so the terminal 22 will not also interfere with X-ray photography that may be performed on the patient.

A platform component 34 is cantilevered from the body's front end 16 and made integral with the body's top surface. A portion of the terminal 22 is interposed between the platform 34 and the body 14. A substantially rectangular cavity 36, having a back wall 37, is disposed in a center region of a front end 38 of the platform 34. The platform 34 includes elongated guide ribs 40 disposed on either side that extend parallel to the longitudinal axis of the body 14. The platform component 34 may have a plate 42 disposed on a portion of its top surface to accommodate the lead wire 30 coupling to the terminal 22.

Figure 6:
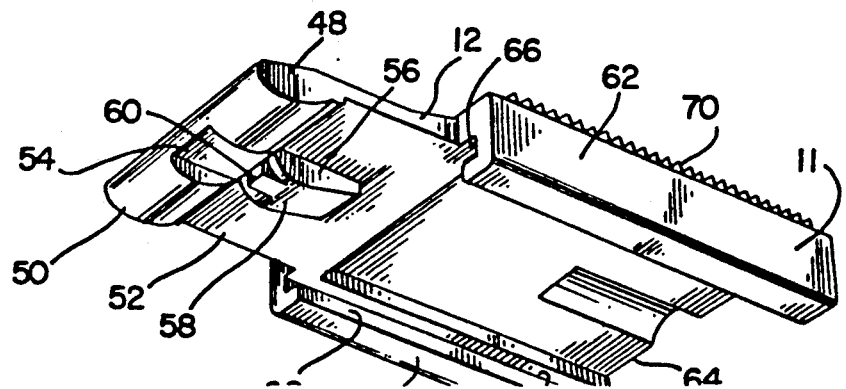
FIG. 6 is a bottom perspective view of an actuator of the preferred embodiment of the present invention.

FIG. 6 shows a bottom perspective view of the actuator component 12 of the preferred embodiment. The elongated actuator 12 has a front end 48 of a curvilinear configuration that defines a second camming surface 50. The second camming surface 50 is located adjacent to a bottom surface 52 of the actuator 12. The second camming surface 50 includes a depression 54 located in its center region. A stop member 56 is disposed adjacent to the second camming surface's depression 54. The stop member 56 may have a partially pitched bottom surface 58 to aid the attaching of the actuator 12 to the body 14. The stop member 56 also includes a substantially flat front edge 60 that abuts the terminal's teeth 28 when the connector 10 is in the overcenter locked position. The actuator 12 may be molded from any suitable rigid medical grade plastic that is X-ray transparent, such as ABS plastic.

A coupling portion 11 is cantilevered from the front end 48. The coupling portion 11 includes a downwardly-projecting, elongated flange 62 disposed on either side. In the preferred embodiment, the guide flanges 62 are substantially the same length as the platform's guide ribs 40. Each flange 62 has a rectangular groove 66 that extends the length of its interior side 68 to the rear end 64. The grooves 66 are a configuration complementary to the ribs 40 to slidably engage the ribs 40 for slidably coupling the actuator 12 substantially parallel to the body 14.

In an alternative embodiment (not shown), the coupling portion's flanges 62 may have guide ribs that extend the length of the interior sides 68. The platform 34 may then have grooves disposed on either side that extend parallel to the longitudinal axis of the body 14. This configuration would enable the actuator 12 to slidably couple substantially parallel to the body 14.

Referring now to FIGS. 1 through 4, the connector 10 is in its open position (shown in FIG. 2). The open position is defined by sliding the actuator 12 rearwardly, until the stop member 56 abuts the back wall 37 of the platform's cavity 36. A portion 29 of the conductive flexible electrode 31 is placed between the body's front end 16 and the actuator's front end 48. The actuator 12 is then slid forwardly with the respective front ends 16, 48 of the body 14 and actuator 12 flexing as the camming surfaces 18, 50 coact to grasp the electrode's portion 29, until the second camming surface 50 extends beyond the apex 26 of the first camming surface 18. When the actuator 12 is slid to its forwardmost position in relation to body 14, the second camming surface 50 extends over the first camming surface's apex 26. A substantially sinusoidal interface is defined between the second camming surface 50 and first camming surface 18 when the actuator 12 is in the overcenter position or locking position.

Figure 4:
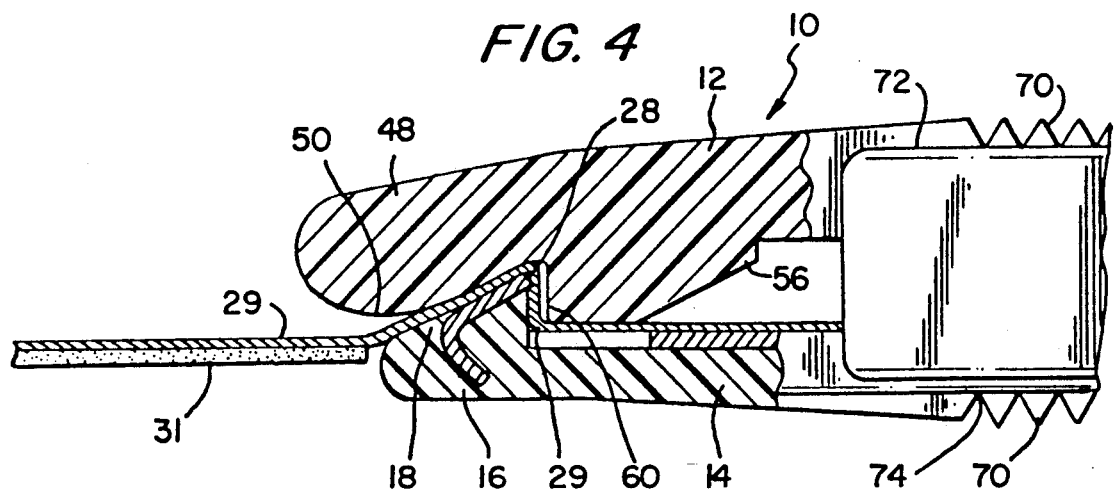
FIG. 4 is a partial breakaway view.

As seen in FIG. 4, with the connector 10 in the closed position, the stop member's front edge 60 forces the electrode's portion 29 into the notch 20, while the electrode 31 is frictionally engaged between the second camming surface 50 and the first camming surface 18. The stop member 56 maintains the actuator 12 in the overcenter locking position. Thus, the first and second camming surfaces 18, 50 frictionally engage the conductive flexible electrode 31 and bring it into electrical contact with the terminal 22. The terminal's teeth 28 extend slightly into the electrode's portion 29 to enhance electrical contact and prevent the connector 10 from detaching from the electrode 31. The terminal's teeth 28 and frictional engagement by the first 18 and second 50 camming surfaces also prevent the electrode from rotating about the sinusoidal interface that may result in instrumental artifact when the connector 10 is attached to the electrode 31.

The conductive electrode's portion 29 may be released from the connector 10 by sliding the actuator 12 rearwardly, to the open position, thus disengaging the teeth 28 from the electrode's portion 29 and releasing the conductive portion 29 from its assumed sinusoidal configuration.

A plurality of ridges 70 may be disposed latitudinally across a top surface 72 of the actuator 12 and a bottom surface 74 of the body 14. The ridges 70 aid in gripping the connector 10 when sliding the actuator 12 for opening and closing the connector 10.

The body's first end 16 and actuator's front end 48 enable the electrical connector 10 to attach to a number of different flexible electrodes of varying designs. The slidable configuration of the electrical connector 10 result in a connector that is low profile, thus not a discomfort t patients, and a connector that is easy to use by a simple sliding action.

While the above features of the present invention teach method, apparatus, and an improved electrical connector, it can be readily appreciated that it would be possible to deviate from the above embodiments of the present invention and, as will be readily understood by those skilled in the art, the invention is capable of many modifications and improvements within the scope and spirit thereof. Accordingly, it will be understood that the invention is not to be limited by the specific embodiments, but only by the spirit and scope of the appended claims.

What is claimed is:

1. A biomedical electrical connector for a flexible electrode comprising:
   means for conducting electrical potential;
   a body assembly for holding the conducting means, the body assembly including a first camming means of a substantially convex protrusion extending substantially across a width of a front end thereof, and
   actuator means, slidably coupled to the body assembly, for detachably connecting the electrical connector to the flexible electrode, the actuator means being slidable substantially parallel to a longitudinal axis of the body assembly, the actuator means including a second camming means of a substantially convex protrusion extending substantially across a width of a front end thereof, the first and second camming means capable of interacting to provide an overcenter locking position while deforming a portion of the flexible electrode interposed between the body assembly and the actuator means when the actuator means is slid to a forwardmost position in relation to the body assembly, for attaching the electrical connector to the flexible electrode and to conductively couple the flexible electrode to the conducting means.

2. The biomedical electrical connector of claim 1, wherein the body assembly includes a rear platform component having guide ribs disposed on either side that extend substantially parallel to the longitudinal axis of the body assembly.

3. The biomedical electrical connector of claim 2, wherein the actuator means has a coupling portion that extends parallel to a longitudinal axis thereof, the coupling portion including elongated downwardly-projecting guide flanges disposed on either side, each flange having a channel in an interior side complementary to the configuration of the guide ribs to slidably engage the guide ribs of the platform component for slidably coupling the actuator means substantially parallel to the body assembly.

4. The biomedical electrical connector of claim 3, wherein the first and second camming means defining a substantially sinusoidal interface between the front end of the actuator means and the front end of the body assembly when the actuator means is slid generally forwardly in relation to the body assembly, the second camming means extending over the first camming means to an overcenter position, and the sinusoidal interface deforming the portion of the flexible electrode by frictionally engaging the portion of the flexible electrode.

5. The biomedical electrical connector of claim 4, wherein the conducting means comprises a flat terminal disposed on a top surface of the body assembly and interposed between the body assembly and the platform component, and the terminal has a plurality of teeth projecting outwardly from a center of an apex of the first camming means and at an acute angle to the longitudinal axis of the body assembly for conductively coupling the terminal to the flexible electrode when the electrode is frictionally engaged in the sinusoidal interface.

6. The biomedical electrical connector of claim 5, further including a notch located in the center region of the first camming means, a cavity located at a center region of a front end of the platform component adjacent to the front end of the body assembly, and a stop means affixed to a bottom surface of the actuator means adjacent to a center region of the second camming means, the stop means abutting a back wall of a cavity when the actuator means is slid generally rearwardly in relation to the body assembly for limiting the rearward horizontal travel of the actuator means in relation to the body assembly, and abutting the plurality of teeth of the terminal when the actuator means is slid generally forwardly in relation to the body assembly to extend a portion of each of the plurality of teeth into the flexible electrode to conductively couple the terminal to the flexible electrode.

7. The biomedical electrical connector of claim 6, wherein the terminal is coupled to a conductive lead wire for outputting electrical potential.

8. A medical electrical connector for a flexible electrode, comprising:
   a body member including a platform component having a guide rib disposed on either side extending substantially parallel to the longitudinal axis of the body member;
   a layer of conductive material disposed on the body member and interposed between the body member and the platform component;
   an actuator member having downwardly-projecting guide flanges disposed on either side of a coupling portion, each guide flange having a groove in an interior side of a complementary configuration to the guide ribs to slidably engage the guide ribs of the platform component for slidably coupling the actuator member substantially parallel to the longitudinal axis of the body member, and couple means provided on a front end of the body member and a front end of the actuator member for detachably coupling the connector to a flexible electrode, including a first protrusion extending across a width of the front end of the body member defining a first camming surface, and a second protrusion extending across a width of the front end of the actuator member defining a second camming surface, the first and second camming surfaces defining a sinusoidal interface between the front end of the actuator member and the front end of the body member when the actuator member is slid generally forwardly in relation to the body member, the second camming surface extending over the first camming surface to an over-center position, the sinusoidal interface frictionally engaging a portion of the flexible electrode to prevent the connector from detaching from the flexible electrode.

9. The medical electrical connector of claim 8, wherein the layer of conductive material comprises a flat terminal affixed to a top surface of the body member and interposed between the body member and the platform component, the terminal having a plurality of teeth projecting outwardly from a center region of an apex of the first camming surface at an acute angle to the longitudinal axis of the body member for conductively coupling the terminal to the flexible electrode when the electrode is frictionally engaged by the sinusoidal interface.

10. The medical electrical connector of claim 9, further comprising a notch located at a center region of the first camming surface and a cavity located at a center region of a front end of the platform component adjacent to the front end of the body member, and a stop member affixed to a bottom surface of the actuator member adjacent to a center region of the second camming surface, the stop member abutting a back wall of the cavity when the actuator member is slid generally rearwardly in relation to the body member for limiting the rearward horizontal travel of the actuator member in relation to the body member, and abutting the plurality of teeth of the terminal when the actuator member is slid generally forwardly in relation to the body member to extend a portion of each of the plurality of teeth into the flexible electrode to conductively couple the terminal to the flexible electrode.

11. The medical electrical connector of claim 10, wherein the terminal is connected to a conductive lead wire to output electrical potential.

12. The medical electrical connector of claim 11, wherein the terminal comprises an electrically conductive, X-ray translucent material 13. The medical electrical connector of claim 12, wherein the body member and actuator member comprise rigid, X-ray transparent, medical grade plastic.

14. The medical electrical connector of claim 13, wherein a plurality of ridges are latitudinally disposed on a bottom surface of the body member and a top surface of the actuator member.

15. A biomedical electrical connector for a flexible electrode, comprising:
a body member including a rear platform component having guide ribs disposed on either side thereof that extend substantially parallel to a longitudinal axis of the body member;
a conductive terminal disposed on the body member and interposed between the body member and the platform component, the terminal having a plurality of teeth projecting outwardly from an apex of a curvilinear front end of the body member and at an acute angle to the longitudinal axis of the body member, and
an actuator member having a coupling portion and a front end of a curvilinear configuration cantilevered from the coupling portion, the coupling portion including downwardly-projecting guide flanges disposed on either side, each flange having a groove in an interior side of a configuration complementary to the guide ribs to slidably engage the guide ribs of the platform component for slidably coupling the actuator member substantially parallel to the longitudinal axis of the body member, a sinusoidal interface being defined between the front of the actuator member and a front end of the body member when the actuator member is slid generally forwardly in relation to the body member until the front end of the actuator member extends over the front end of the body member to an overcenter position, the front ends of the actuator member and the body member flexing to accommodate the curvilinear configurations thereof;
whereby, when a portion of a flexible electrode is placed between the front end of the actuator member and the front end of the body member and the actuator member is slid to its overcenter position, the portion of flexible electrode is frictionally engaged by the sinusoidal interface of the body member and the actuator member and brought into electrical contact with the terminal, the teeth of the terminal extending into the portion of electrode to electrically couple the electrode to the terminal and to prevent the connector from detaching from the flexible electrode.

16. The biomedical electrical connector of claim 15 wherein the terminal comprises an electrically conductive, X-ray translucent terminal and is connected to a conductive lead wire having a substantially thin ribbon of copper extending therethrough for outputting electrical potential.

17. The biomedical electrical connector of claim 16 wherein the body member comprises a rigid, electrically conductive, X-ray translucent, medical grade plastic and the actuator member comprises a rigid, X-ray transparent, medical grade plastic.

18. The biomedical connector of claim 17 wherein a plurality of ridges are disposed on a bottom surface of the body member and a top surface of the actuator member.

19. A medical electrical connector, comprising:
a flat elongated body member including a substantially convex protrusion extending across a width of a front end defining a first camming surface, the first camming surface disposed on a top surface of the body member and having a notch disposed in its center region, the body member including a platform located on the top surface that extends from a back end of the body member towards the front end of the body member and includes a notch located in a center region of a front end of the platform adjacent to the front end of the body member, the platform including a guide rib disposed on either side that extend parallel to the longitudinal axis of the body member;
an electrically conductive terminal disposed on a top surface of the body member extending substantially from an apex of the first camming surface and along the length of the body member, the terminal having a plurality of teeth projecting outwardly from the apex of the first camming surface adjacent to the notch and at an acute angle to the longitudinal axis of the body member, the terminal coupled to an electrical wire adjacent to the back end of the body member;

an elongated actuator member having a convex protrusion extending across a width of a front end of a bottom surface defining a second camming surface, the first and second camming surfaces defining a sinusoidal interface between the front end of the actuator member and the front end of the body member when the actuator member is slid to a forwardmost position in relation to the body member, the second camming surface including a depression in its center of a configuration complementary to the projecting teeth, the actuator member having a stop member disposed adjacent to the depression in the second camming surface, the actuator member including a coupling portion comprising a pair of downwardly-projecting elongated flanges, one each disposed on either side of the actuator member and extending from a back end of the actuator member towards the front end, each flange having a groove in an interior side extending along its length to slidably engage the guide ribs of the platform for slidably coupling the actuator member substantially parallel to the longitudinal axis of the body member, whereby, when a portion of a flexible electrode is placed between the front end of the actuator member and the front end of the body member and the actuator member is slid to its forwardmost position, the portion of flexible electrode is frictionally engaged by the sinusoidal interface of the body member and the actuator member and is brought into a sinusoidal configuration with the teeth of the terminal extending into the portion of electrode to prevent the connector from detaching from the flexible electrode and for conductively coupling the electrode to the terminal.

* * * * *